United States Patent [19]

Masaki

[11] Patent Number: 4,834,701
[45] Date of Patent: May 30, 1989

[54] APPARATUS FOR INDUCING FREQUENCY REDUCTION IN BRAIN WAVE

[75] Inventor: Kazumi Masaki, Osaka, Japan

[73] Assignee: Ken Hayashibara, Okayama, Japan

[21] Appl. No.: 758,534

[22] Filed: Jul. 24, 1985

[30] Foreign Application Priority Data

Aug. 24, 1984 [JP] Japan .................. 59-175098

[51] Int. Cl.⁴ .............................................. A61N 1/34
[52] U.S. Cl. ...................................................... 600/28
[58] Field of Search .................. 128/731–732, 128/905, 1 C, 1 R; 600/26–28

[56] References Cited

U.S. PATENT DOCUMENTS

| | | | |
|---|---|---|---|
| 3,489,843 | 1/1970 | Schrecongost | 84/1.24 |
| 3,712,292 | 1/1973 | Zentmeyer, Jr. | 128/1 C |
| 3,799,146 | 3/1974 | John et al. | 128/731 |
| 3,809,069 | 5/1974 | Bennett | 128/731 |
| 4,092,981 | 6/1978 | Ertl | 128/731 |
| 4,141,344 | 2/1979 | Barbara | 128/1 C |
| 4,191,175 | 3/1980 | Nagle | 128/1 C |
| 4,227,516 | 10/1980 | Meland et al. | 128/1 C |
| 4,289,121 | 9/1981 | Kupriyanovich | 128/1 C |
| 4,315,502 | 2/1982 | Gorges | 128/1 C |
| 4,323,079 | 4/1982 | Demetrescu | 128/731 |
| 4,334,545 | 6/1982 | Shiga | 128/732 |
| 4,335,710 | 6/1982 | Williamson | 128/1 C |
| 4,388,918 | 6/1983 | Filley | 128/1 C |
| 4,550,736 | 11/1985 | Broughton et al. | 128/731 |
| 4,573,449 | 3/1986 | Warncke | 128/1 C |

FOREIGN PATENT DOCUMENTS

| | | | |
|---|---|---|---|
| 1554569 | 1/1969 | France | 128/1 C |
| 1392893 | 5/1975 | United Kingdom . | |
| 1451019 | 9/1976 | United Kingdom . | |
| 2067410 | 7/1981 | United Kingdom . | |
| 2124491 | 2/1984 | United Kingdom . | |

Primary Examiner—Kyle L. Howell
Assistant Examiner—Angela D. Sykes
Attorney, Agent, or Firm—Browdy and Neimark

[57] ABSTRACT

Frequency reduction in human brain wave is inducible by allowing human brain to perceive 4–16 hertz beat sound. Such beat sound can be easily produced with an apparatus, comprising at least one sound source generating a set of low-frequency signals different each other in frequency by 4–16 hertz. Electroencephalographic study revealed that the beat sound is effective to reduce beta-rhythm into alpha-rhythm, as well as to retain alpha-rhythm.

13 Claims, 3 Drawing Sheets

$A_1, A_2, A_3$ = FREQUENCY LOWERING CIRCUITS

APPARATUS FOR INDUCING FREQUENCY REDUCTION IN BRAIN WAVE

FIELD OF THE INVENTION

The present invention relates to an apparatus to induce frequency reduction in human brain wave.

DESCRIPTION OF THE PRIOR ART

The human brain wave produced when the five sensory organs are in action is called as "beta-rhythm", a brain wave of 15 hertz or higher, which is reduced to the "alpha-rhythm", a brain wave of 7 to 14 hertz, by mental relaxation.

One may exhibit an amazing ability when one's brain wave is in alpha-rhythm. In such state, a great ability may be exhibited in learning, researching, and making invention.

So far no effective means to induce frequency reduction in human brain wave was proposed.

SUMMARY OF THE INVENTION

Accordingly, one general object of the invention is to provide an apparatus to induce frequency reduction in human brain wave.

Still more specific object of the invention is to provide an apparatus to allow human brain to perceive a beat sound within a prescribed frequency range.

These and other objects as may become apparent hereafter have been attained with an apparatus, comprising means for generating a pair of low-frequency signals; said signals being different in frequency by 4–16 hertz.

BRIEF DESCRIPTION OF THE DRAWING

The present invention will hereinafter be explained with reference to the accompanying drawings.

In the Figures, F indicates oscillator; SP, loudspeaker; IC, linear integrated circuit; C, capacitance; R, resistance; A, frequency lowering-circuit; B, waveform-modifier; D, decade counter; and S, switch.

DESCRIPTION OF THE PREFERRED EMBODIMENTS

Figure 1:
FIG. 1 show a basic structure of an apparatus according to the invention.

FIG. 1 shows a basic structure of an apparatus according to the invention, wherein the outputs of first- and second-oscillators $F_1$ and $F_2$ are sounded with loudspeakers $SP_1$ and $SP_2$ respectively. The ears perceive their frequency difference as beat. Human brain wave can be reduced to alpha-rhythm by employing a beat frequency approximate or equal to alpha-rhythm.

Figure 2:
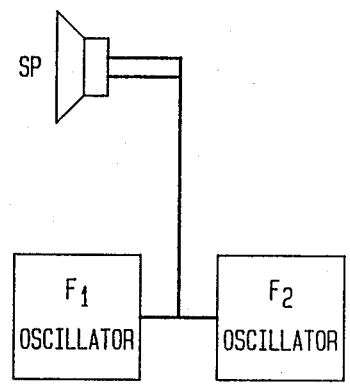
FIG. 2 shows another basic structure using single sound source.

FIG. 2 shows an example wherein the outputs of first- and second-oscillators $F_1$ and $F_2$ are sounded with single loudspeaker SP.

Figure 3:
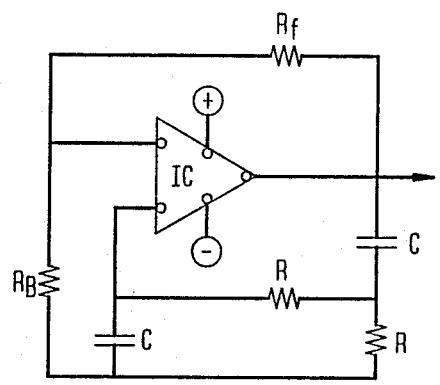
FIG. 3 shows a circuit diagram of an oscillator feasible in the invention.

FIG. 3 illustrates an oscillator circuit, essentially consisting of linear integrated circuit IC, capacitance C and resistance R, feasible in first- and second-oscillators $F_1$ and $F_2$. The oscillation frequency f is expressed by $f=1/\kappa RC$, where $\kappa$ is the constant. In the apparatus according to the invention, the oscillation frequency f is generally set to 120–180 hertz.

Figure 4:
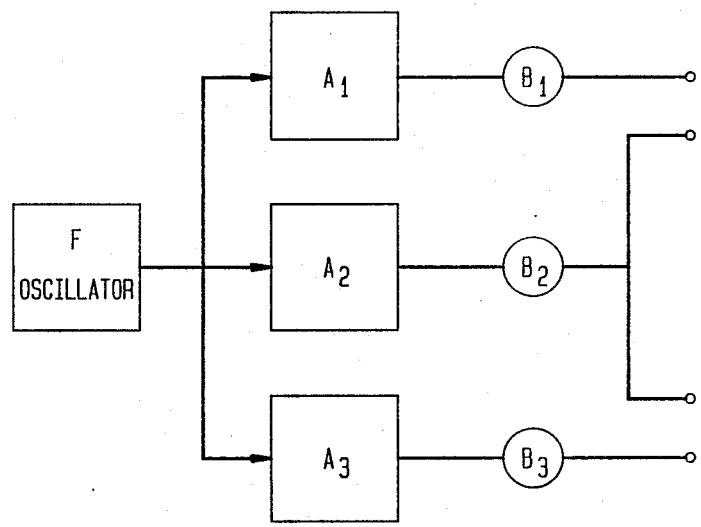
FIG. 4 shows a circuit diagram of an apparatus feasible to generate a correct frequency difference.

FIG. 4 shows a means for fixing the frequency difference in order to obtain a stabilized beat. For example, 900 hertz fundamental frequency, produced by oscillator F, is applied to frequency lowering-circuits $A_1$, $A_2$ and $A_3$ to obtain signal with one-ninth, one-eighth or one-seventh of the fundamental frequency, i.e. 100, 112.5 and 128 hertz, respectively. These signals are changed by waveform-modifiers $B_1$, $B_2$ and $B_3$ into more audible signals, and then used to generate a beat sound corresponding to either frequency difference of $112.5-100=12.5$ (hertz) or $128-112.5=15.5$ (hertz).

Figure 5:
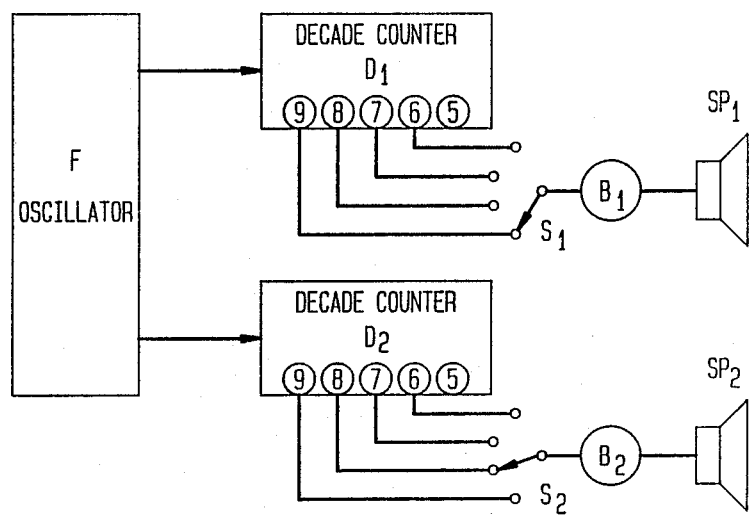
FIG. 5 shows a circuit diagram wherein decade counters are used.

FIG. 5 shows an example wherein fundamental frequency f produced by oscillator F is lowered by decade counter F. Decade counter F is arranged to produce single synchronous signals at output terminals 9, 8, 7 and 6 for every ninth-, eighth-, seventh- or sixth-cycles of the fundamental frequency. For example, when oscillator F is supposed to generate 900 hertz signal, then 100 hertz signal appears at output terminal 9 of decade counter $D_1$. Similarly, output terminal 8 of decade counter $D_2$ is applied with 112.5 hertz signal; terminal 7, 128.5 hertz signal; and terminal 6, 150 hertz signal. By turning an output terminal 9 of decade counter $D_1$ and output terminal of 8 of decade counter $D_2$ with switches $S_1$ and $S_2$, a 12.5 hertz beat sound is produced, while by using output terminal 9 of decade counter $D_1$ and output terminal 7 of decade counter $D_2$ a 28.5 hertz beat is sounded. A beat sound with a desirable frequency, obtained by turning on any two output terminals with switches $S_1$ and $S_2$, is changed with waveform-modifiers $B_1$ and $B_2$ into a more audible signal, and then sounded by loudspeakers $SP_1$ and $SP_2$.

Figures 6, 7:
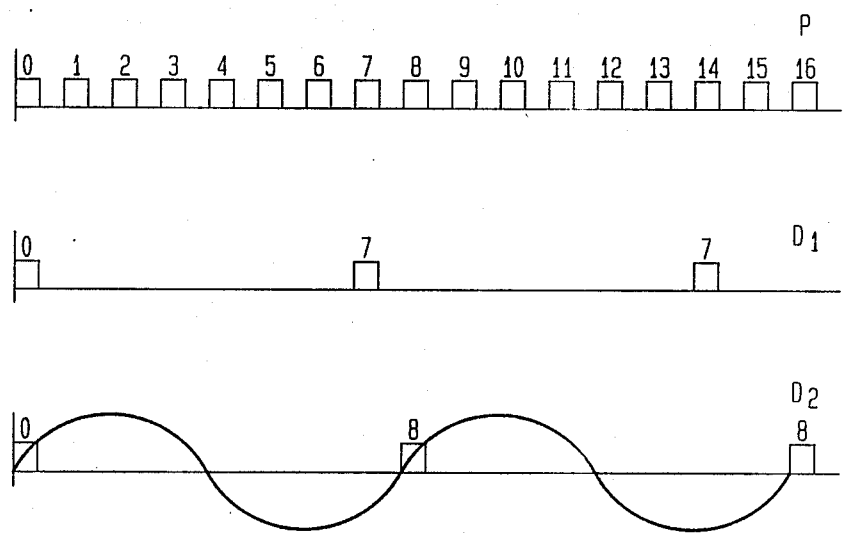
FIG. 6 shows the frequency of human brain waves.
FIG. 7 shows a waveform chart illustrating frequency lowering operation of decade counter.

FIG. 6 shows the frequency of human brain waves: It can be seen that the frequency of human brain wave produced when the five sensory organs are in action is 15 hertz or higher, but shiftable to alpha-rhythm, i.e. 7-14 hertz, by mental relaxation.

FIG. 7 shows the operations of decade counter D. When successive signals 0, 1, 2, . . . , and 16 come into decade counters $D_1$ and $D_2$ in a manner as shown with chart "P", for example, seventh- and eighth-signal 7 and 8 produce single pulses at decade counters $D_1$ and $D_2$ respectively to back them to the first state for the subsequent counting. By using these as synchronous signal, sine or other suitable waveform can be desirably generated, followed by modification into a more audible waveform with waveform-modifier B.

An electroencephalographic study using volunteers confirmed that 4-16 hertz beat sound is most effective to lower the frequency of human brain wave to 8-14 hertz alpha-rhythm. I found that such beat sound is also effective to retain alpha-rhythm, as well as to bring human brain wave from either "theta-rhythm" or "delta-rhythm" into alpha-rhythm.

Having described the present invention as related to the embodiments shown in the accompanying drawings, it is my intention that the invention is not limited by any of the details of description, but rather be construed broadly within its spirit and scope as set out in the accompanying claims.

I claim:

1. An apparatus for inducing frequency reduction of human brain wave, comprising:
   (a) means for generating a first low-frequency signal which is higher in frequency than the range of 4 to 16 hertz;
   (b) means for generating a second low-frequency signal which is higher in frequency than the range of 4 to 16 hertz and is different in frequency by 4 to 16 hertz from the first signal;
   (c) means for sounding the first- and second signals to generate a beat signal of the frequency of 4 to 16 hertz.

2. The apparatus in accordance with claim 1, wherein the frequency of the first signal is 120 to 180 hertz.

3. The apparatus in accordance with claim 1, wherein either or both of said generating means comprises a means for generating a low-frequency signal and a means for lowering the frequency of the signal.

4. The apparatus in accordance with claim 3, wherein said frequency lowering means is coupled with the sounding means through a waveform-modifier.

5. The apparatus in accordance with claim 3, wherein said frequency lowering means is a decade counter.

6. The apparatus in accordance with claim 1, wherein said sounding means is at least one earphone or loudspeaker.

7. The apparatus in accordance with claim 1, wherein said generating means essentially consists of a linear integrated circuit, capacitance, and resistance.

8. An apparatus for inducing frequency reduction of brain waves of human subject, comprising:
   (a) first means for generating a first low-frequency signal which is higher in frequency than the range of 4 to 16 hertz;
   (b) second means for generating a second low-frequency signal which is higher in frequency than the range of 4 to 16 hertz and is different by 4 to 16 hertz from said first low-frequency signal; and
   (c) means for sounding said first- and second-low frequency signals to generate a beat signal of the frequency of 4 to 16 hertz;
   whereby upon perceiving said beat signal by the human brain the ongoing state of brain wave is shifted to alpha-rhythm.

9. The apparatus of claim 8, wherein at least one of said first and second generating means comprises a third means for generating a third low-frequency signal and a means for lowering the frequency of said third low-frequency signal to produce a fourth low-frequency signal.

10. The apparatus of claim 9, wherein said means for lowering said third low-frequency signal is coupled with said means for sounding through a waveform-modifier.

11. The apparatus of claim 10, wherein said means for lowering comprises a decade counter.

12. The apparatus of claim 8, wherein said means for sounding is coupled to at least one ear of the human subject.

13. The apparatus of claim 8, wherein each of said means for generating a first- and a second- low frequency signal comprises linear integrated amplifier means, capacitor means, and resistor means.

* * * * *